(12) United States Patent
Komi

(10) Patent No.: US 6,491,627 B1
(45) Date of Patent: Dec. 10, 2002

(54) MANIPULATION MECHANISM FOR AN ANGLE SECTION OF AN ENDOSCOPE

(75) Inventor: Shuji Komi, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 143 days.

(21) Appl. No.: 09/640,193

(22) Filed: Aug. 17, 2000

(30) Foreign Application Priority Data

Aug. 18, 1999 (JP) ............................................. 11-231237
Aug. 18, 1999 (JP) ............................................. 11-231238

(51) Int. Cl.[7] ................................................. A61B 1/00
(52) U.S. Cl. ........................................ 600/146; 600/149
(58) Field of Search ................................ 600/146, 147, 600/148, 149, 150; 604/95.01, 95.04

(56) References Cited

U.S. PATENT DOCUMENTS

| 3,892,228 A | * | 7/1975 | Mitsui | 600/142 |
| 4,294,233 A | * | 10/1981 | Takahashi | 403/43 |
| 4,483,326 A | * | 11/1984 | Yamaka et al. | 600/141 |
| 5,667,476 A | * | 9/1997 | Frassica et al. | 600/139 |

* cited by examiner

*Primary Examiner*—Linda C. M. Dvorak
*Assistant Examiner*—Kenneth Schopfer
(74) *Attorney, Agent, or Firm*—Oblon, Spivak, McClelland, Maier & Neustadt, P.C.

(57) ABSTRACT

A manipulation mechanism for an angle section of an endoscope includes at least one pulley provided within a main operation unit, with the base ends of a pair of operating wires wound thereupon, a pulley rotating shaft extended externally from a casing of the main operation unit to rotate the pulley, an angle operating apparatus provided outside of the main operation unit and coupled to the pulley rotating shaft, a pulley supporting assembly fixedly held by the casing of the main operation unit for supporting the pulley to be reciprocally rotated over a predetermined angle, a sleeve member provided within the main operation unit for passing through the operating wires from the pulley, a pipe holder fixedly mounted to the sleeve member, and a supporting rod connected at one end to the pulley supporting assembly and being fixed to the pipe holder at the other end.

13 Claims, 13 Drawing Sheets

MANIPULATION MECHANISM FOR AN ANGLE SECTION OF AN ENDOSCOPE

DETAILED DESCRIPTION OF THE INVENTION

1. Technical Field of the Invention

The present invention relates to a mechanism for manipulating an angle section in an insertion portion of an endoscope used for use in medial and other fields.

2. Description of the Related Art

An endoscope for medical or other use, generally, consists mainly of an insertion portion to be inserted into a body cavity and the like, a main operation unit to be connected at the base end of the insertion portion, and a universal cord which is extended from the main operation unit and is detachably connected to at least a light source device. The insertion portion is adapted to be inserted into the body cavity of a patient or the like for inspecting and carrying out diagnosis inside the body. Further, when necessary, a treatment can be performed by using forceps, a high-frequency treatment or other treating equipment to be inserted into the endoscope.

An operator manipulating the endoscope usually holds the main operating unit with one hand. In order to reduce a load on the operator operating the endoscope, the main operation unit is designed to be of reduced weight. To this end, the casing of the operation unit is formed of plastic, and the thickness of the casing is reduced as much as possible to expand the internal space with a small and compact shape. Since various members are installed within the operation unit, its casing is divided into several parts. These parts can be detachably assembled for the convenience of maintenance to those installed members, such as mounting, repair, inspection and replacement.

The casing of the main operation unit must have sufficient strength, at least part to which the manipulating or operating mechanism such as the later-described angle operation device is fixedly mounted. Therefore, the casing comprises a thick-walled main unit case portion to which is mounted the angle operation device and the like. The main operation unit has a main unit case portion and other portion or portions such as a holding case portion held by the operator. The holding case portion and the like are formed with thin-walled plastic, and may not be as strong as the main unit case portion.

A connecting member made of metal or the like mounted which is provided in the casing of the main operation unit is known in Japanese Patent Publication No. 2-43484. The known connecting member functions as a framework for the assembled parts of the casing to reinforce high strength. With this known configuration, the connecting member with the metal plate has one end fixed to the main unit case portion, and is extended to at least the inside of the holding case portion. The connecting member is fixed in a manner to exert a force to the holding case and the like to pull tightly, thereby abutting against the main unit case portion, and thereby increasing the overall strength of the casing of the main operation unit.

The insertion portion has a distal end section and an angle section, and further there is a bending section provided between the angle section and the operation unit. An endoscopic observing mechanism consisting of an illumination window and an observation window are provided at the distal end section. A treatment equipment outlet for introducing treatment equipment such as forceps is also provided at the distal end section as necessary. The angle section functions to turn the distal end section toward a desired direction by performing an angle operation to curve or flex it in vertical and horizontal directions by a remote control mechanism. Operating wires are provided to enable this angle operation. At least one pair of operating wires is provided at the upper and lower places in the insertion section for curving or flexing at a desired angle for the angle section vertically in the event that one operating wire is pulled and the other is pushed. Further, in addition to the pair each of the operating wires for upper and lower portions, another pair of operating wires is provided at the right and left places, thereby the angle section may be induced to curve vertically and horizontally. These operating wires are extended from the insertion portion to the inside of the main operation unit, and are connected to an angle operation device mounted to this main operation unit.

The angle operation device has at least one pulley, to which the base portions of the operating wires are wound, to pull and push the pair of the operating wires by rotation (one pulley uses a pair of operating wires, and two pulleys use two pairs of operating wires). A rotating shaft is coupled to the pulley. This rotating shaft is extended externally from the casing of the operation unit and an angle operation means, such as a knob or a lever, is linked thereto. The operator can control the direction of the angle section by manually manipulating the angle operating means using the fingers of the hand holding the operation unit.

The operating wires for angle operation are, for example, control cables, and a predetermined length of each operation wire is passed through the sleeve member. Thus, pushing and pulling the base end transmits the force thereof to the tip end. The sleeve member is generally flexible, such as a tightly coiled wire and flexible sleeve, or the like. However, at the rigid portion in the endoscope, for example, within the main operation unit, the sleeve member can be made of a hard pipe. Opposite ends of the sleeve member are to be securely fixed, and the operating wires are drawn out from both ends of the fixed sleeve member. The base end of the operating wire is wound around the pulley. The tip end of the operating wire is taken out from the sleeve member, which is provided at or before the angle section.

A great reaction force acts on the operating wires at the time of angle operation and this reaction force is to be received by the pulley. The ends of the sleeve member must be securely fixed, because the fixed portions of the sleeve member are affected by the reaction force. Also, the rotating shaft coupled to the pulley should be supported by the casing of the main operation unit in a stationary manner. The fixing means of the base portion of the sleeve member must also be held in a stable manner. Also, a means for preventing looseness of the operating wires is provided between the sleeve member and the pulley. The means for preventing looseness also moves together with the pushing and pulling operation of the operating wires, so a space is given between the base end of the sleeve member and the pulley to allow the removal of the means for preventing looseness in a predetermined range.

By situating the fixing means of the sleeve member apart from the pulley, the pulley should be connected to the main unit case independently from the edge of the sleeve member. In a conventional manner, the fixing means for the sleeve member is provided within the operation unit, and attached to the connecting member of the casing, which serves as a strength member.

The holding case portion receives a force toward the main operation unit. Also, when the insertion portion is inserted into the body cavity, the connecting member is caused to bend by the force acting to compress the operation unit, by the reaction force caused by the resistance and oppression upon inserting the insertion portion into the body cavity. When the connecting member is bent, the length of the operating wires is changed from the fixing means to the pulley, because the fixing means for the sleeve member is mounted to the connecting member of the casing. As a result, the angle section becomes unintentionally curved slightly even though the angle operating means is not manipulated, the amount of invalid stroke of operating the angle operating means is changed, and so forth.

Also, since the operating wires are exposed between the fixing means of the sleeve member and the pulley, the exposed portions of the operating wires may contact other installed members in the operation unit such as a light guide, thereby resulting in tangling and damage Particularly, in the event that the means for preventing looseness provided to the operating wires is also exposed, the possibility of damage to the light guide formed of, for example, extremely fine optical fibers increases. Further, by separately providing and independently fixing the pulley, the sleeve member fixing means, and a means for guiding the operating wires, it becomes difficult to adjust their relative positional relationships.

In light of the above-mentioned drawbacks of the prior art, it is an object of the present invention to keep tension of the operating wires for performing angle operation constant even if the bending load or the like acts on the main operation unit.

SUMMARY OF THE INVENTION

It is another object of the present invention to maitain a stable positional relationship between the pulley and the sleeve member fixing means.

Further, it is an object of the present invention to allocate the operating wires within the operation unit in a facilitated manner, thereby allowing a smooth and suitable movement of the operation wires.

In accordance with the present invention for achieving the above-mentioned objects, there is provided a manipulation mechanism for an angle section of an endoscope, consisting of a main operation unit and an insert portion connected to the main operation unit, the insert portion having a distal end section connected with the angle section, adapted for manipulating to curve the angle section by pulling and pushing operation at least a pair of operating wires running throughout the insert portion and to introduced into the main operation unit; characterized in that the manipulation mechanism comprises: at least one pulley provided within the main operation unit, with the base of the operating wires wound thereupon; a pulley rotating shaft extended externally from a casing of the main operation unit to rotate the pulley; an angle operating means provided outside of the main operation unit and coupled to the pulley rotating shaft; a pulley supporting assembly fixedly held by the casing of the main operation unit, for supporting the pulley to be reciprocally rotated over a predetermined angle; a sleeve member provided within the main operation unit for passing through the operating wires from the pulley; a pipe holder fixedly mounted to the sleeve member; and a supporting rod connected at one end to the pulley supporting assembly and being fixed to the pipe holder at the other end.

It is desirable to have a wire cover detachably installed on the supporting rod to form a tunnel-shaped passage for running through the operating wires. The casing for the main operation unit can be composed of a main unit case portion to which at least the angle operation means is mounted, and a holding case portion which is assembled to the main unit case portion in a tightly abutting engagement by a connecting member. By so constructing, the fastener member and the supporting rod can be kept apart from the connecting member.

These and other objects, configurations, and advantages of the present invention will become more apparent from the embodiments described below with reference to the drawings. It is needless to say that the present invention is not to be interpreted so as to be restricted to these embodiments.

DESCRIPTION OF THE EMBODIMENTS

Figure 1:
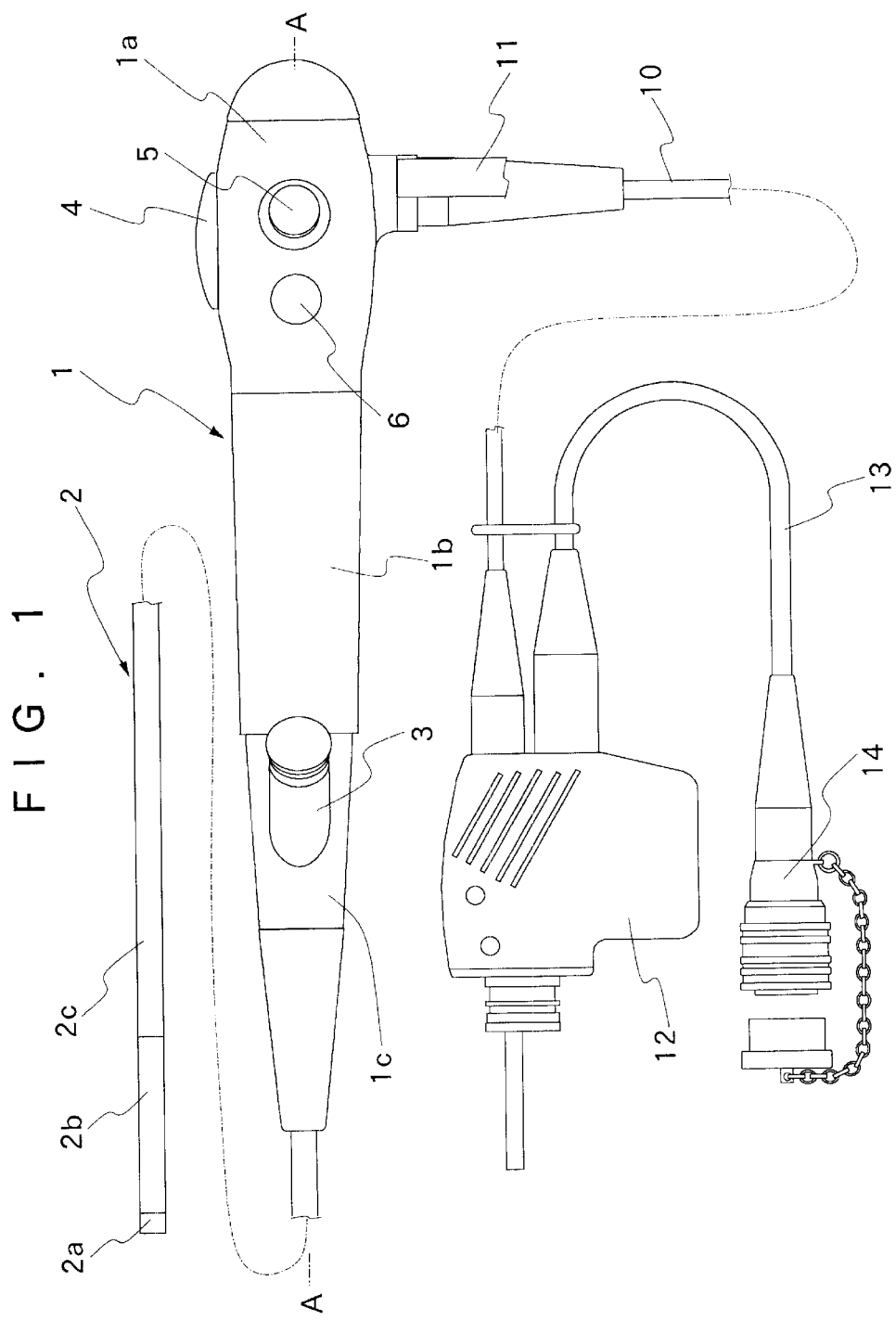
FIG. 1 is an overall configuration diagram of an endoscope illustrating an embodiment of the present invention.

A first embodiment of the present invention will now be described with reference to the drawings. FIG. 1 shows the overall configuration of the endoscope. In this figure, reference numeral 1 denotes a main operation unit, and 2 denotes an insertion portion connected to the main operation unit 1. The insertion portion 2 has a distal end section 2a, an angle section 2b, and a bending section 2c, which are connected to each other side-by-side. Though omitted in the drawings, an endoscopic observing mechanism comprising an illumination window and an observation window is provided to the tip end wall (or tip side wall) of the distal end section 2a. In addition, a treatment equipment outlet is also provided for introducing treatment equipment, such as forceps. The angle section 2b is for turning or flexing the distal end section 2a in the desired direction, and can be curved vertically by a remote control mechanism in the operation unit 1. The bending section 2c is formed of a flexible structure capable of bending in different directions, for example, following the insertion path such as the body cavity or the like.

The operation unit 1 is adapted to be held and handle by the hand of the operator. Normally, the operator holds the operation unit 1 with one hand, and various operating means provided on the operation unit 1 can be manipulated by the fingers of the hand. The operation unit 1 is divided into three mechanism portions. These include: a main unit case portion 1a, a holding case portion 1b, and a forked case portion 1c, provided in that order from the foremost side. The forked case portion 1c at the foremost side constitutes the connecting member to the insertion portion 2, and a treatment equipment introducing portion 3 for introducing treatment equipment. The treatment equipment introducing portion 3 is positioned at the fore side portion of the operation unit 1, i.e., near the insertion portion 2, and a forceps, a high-frequency treatment equipment or the like can be inserted from this treatment equipment introducing portion 3. A treatment equipment passage (not shown) is provided in the insertion portion 2 to communicate the treatment equipment introducing portion 3, and the treatment equipment can be protruded from an opening for outlet of the treatment equipment opened at the tip end of the insertion portion 2. Also, the intermediately positioned holding case portion 1b is the part where the operators hold. Further, various operating means are provided on the main unit case portion 1a positioned at the base side of the operation unit 1.

As for the operating means of the endoscope, an angle operating means 4 is provided for performing curving operation of the angle section 2b in the vertical direction. Also, provided on the upper surface of the main unit case portion 1a are, for example, an operating button 5 for control valves consisting of a suction valve, and an air feeding and water feeding valve, and a freeze switch 6. Further, a VTR (Video Tape Recorder) switch 7 (see FIG. 3) is positioned at the rear end lower portion of the main unit case portion 1a. Note that these switches do not always have to be provided for the operation unit 1, rather, foot switches can be provided for such uses or the switches may be provided directly to the monitor or VTR. Further, even in cases wherein the switches are provided to the operation unit 1, their locations may be chosen arbitrarily, and other operating means besides these may be provided as well.

A universal cord 10 and fluid tube 11 are extended from the operation unit 1. The other end of the universal cord 10 is connected to a light source connector 12, while a cable 13 is extended from the light source connector 12. The other end of this cable 13 is connected to an electric connector 14. Through this configuration, the light source connector 12 is detachably connected to the light source device, and the electric connector 14 is detachably connected to a processor provided either integrally with the light source device or as a separate device. Incidentally, in a case of an optical endoscope it is not necessary to provide the cable 13 and electric connector 14.

Figure 2:
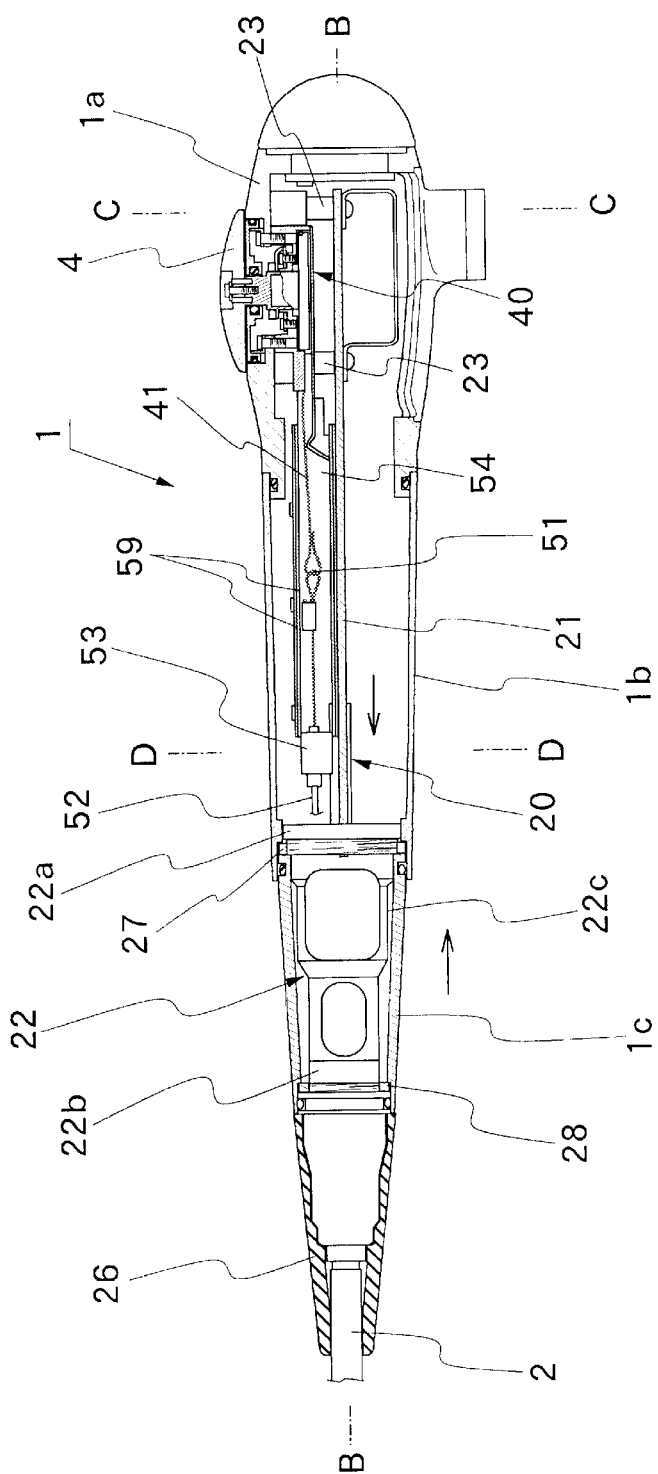
FIG. 2 is a cross-sectional view along line A—A in FIG. 1.
Figure 3:
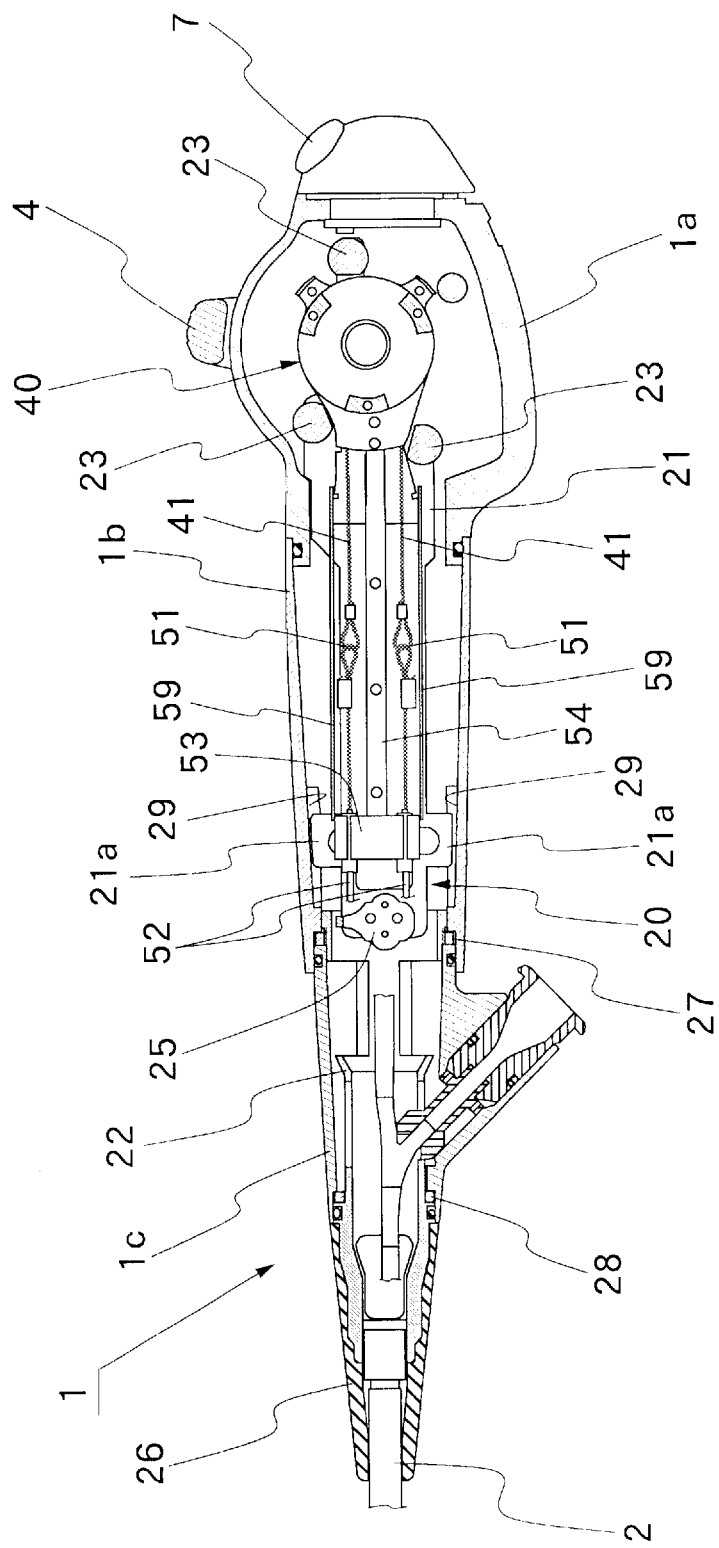
FIG. 3 is a cross-sectional view along line B—B in FIG. 2.
Figure 4:
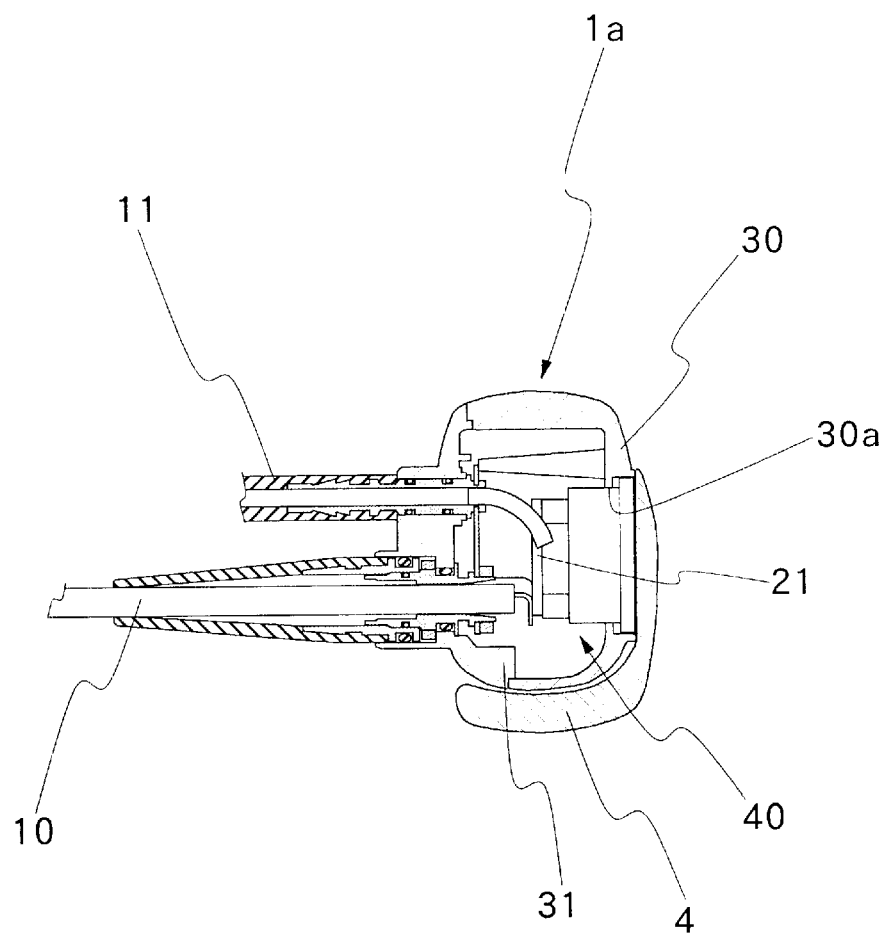
FIG. 4 is a cross-sectional view along line C—C in FIG. 2.

FIG. 2 through FIG. 4 illustrate cross-sections of the operation unit 1. As can be clearly understood from these drawings, the casing formed of the operation unit 1 is made by a plastic in order to reduce its weight. The operation unit 1 comprises three mechanism portions. These three mechanism portions include: a main unit case portion 1a, a holding case portion 1b, and a forked case portion 1c. These three mechanism portions are each formed independently and built in side-by-side in an intimately abutted engagement. The walls of the main unit case portion 1a are thick, while the walls of the holding case portion 1b and forked case portion 1c are thinner. Thus, the weight of the overall operation unit 1 can be reduced, and may also be further reduced in size so as to be compact. The walls of the main unit case portion 1a are thick in consideration of mounting the various operating means, necessitating the property of high-strength in the operation unit 1. The holding case portion 1b and forked case portion 1c are sequentially connected to the main unit case portion 1a in the assembled state.

In order to assemble the casing portions of the operation unit 1, a connecting member 20 is provided within the operation unit 1. The connecting member 20 comprises a connecting plate 21 and a cylindrical holder pipe 22, both formed of metal or the like. The connecting plate 21 and the holder pipe 22 constitute the strength member having a function of the framework of the operation unit 1. The connecting plate 21 extends from inside the main unit case portion 1a to inside of the holding case portion 1b. Then, the connecting plate 21 is joined to the holder pipe 22 at or in the vicinity of the position between the holding case portion 1b and the forked case portion 1c. The holder pipe 22 is placed in from the holding case portion 1b to the forked case portion 1c and protrudes from the fore end of the forked case portion 1c in a predetermined length.

Figure 5:
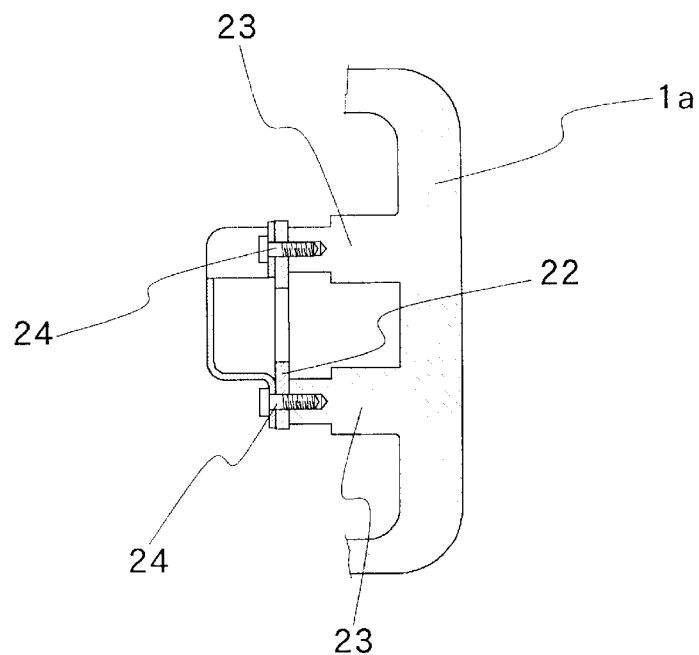
FIG. 5 is a cross-sectional view illustrating the attachment structure of the connecting plate.
Figure 6:
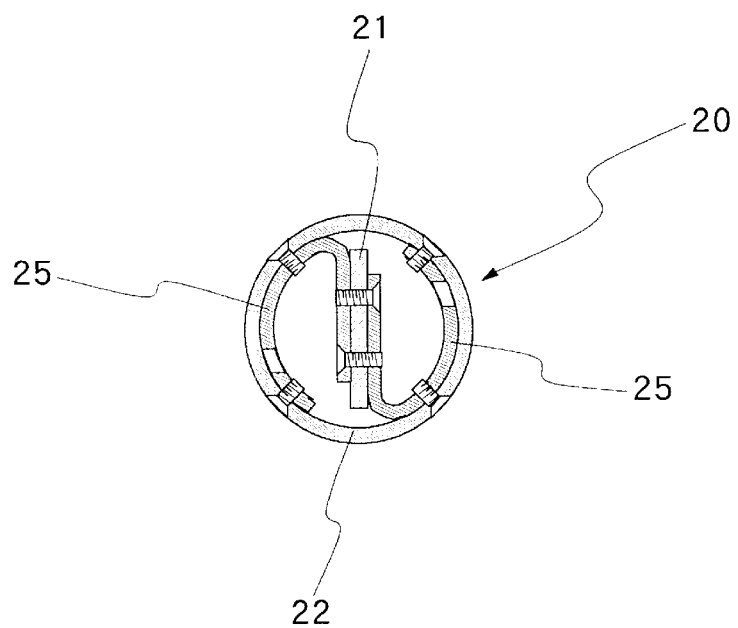
FIG. 6 is a cross-sectional view illustrating the linking structure of the connecting plate and holder pipe.

The base end of the connecting plate 21 of the connecting member 20 is fixed to the main unit case portion 1a. Therefore, as shown in FIG. 5, a plurality of posts 23 (three posts in the embodiment as shown in FIG. 3) are standing out from the inner surface of the main unit case portion 1a. The connecting member 20 is brought into contact with the upper surfaces of the posts 23 and secured by screws 24. Therefore, the connecting plate 21 can be detached from the main unit case portion 1a, and may be assembled in a stable manner. The holder pipe 22 is fixedly connected to the fore portion of the connecting plate 21. The pair of connecting plate pieces 25, 25 are used as the connecting structure, as shown in FIG. 6. These connecting plate pieces 25 have a flat shape at one side to follow the surface of the connecting plate 21, and are inverted from this flat form portion to make a curved shape to coincide with the inner curved surface of the holder pipe 22. Then, the connecting plate piece 25 is fastened by screwing to the connecting plate 21 at the flat shape portion, and to the holder pipe 22 at the curved form part.

The holder pipe 22, which is incorporated into the connecting plate 21, functions to keep the holding case portion 1b intimately abutting against the main unit case portion 1a once assembled. Also, when the forked case portion 1c is attached thereto, the forked case portion 1c is urged toward the main unit case portion 1a by means of the holder pipe 22. Further, the holder pipe 22 serves as a retainer of a cover member 26 made of rubber. The cover member 26 overlays the base portion drawn from the operation unit 1 of the insertion portion 2 to prevent bucking of the outlet portion from the operation unit 1 of the insertion portion 2. Therefore, the generally cylindrical holder pipe 22 is composed of first and second cylinder portions 22a and 22b, and a connecting portion 22c provided between the first and second cylinder portions 22a and 22b. Also, screws are provided to the outer periphery of the first and second cylinder portions 22a and 22b. A stepped wall functioning as a stopper is formed to the inner surface at the fore side of the holding case portion 1b and the forked case portion 1c.

Therefore, the base end of the holding case portion 1b is brought into contact with the main unit case portion 1a, and a screw ring 27 is engaged with the screw portion formed to the first cylinder portion 22a so as to press against a stepped wall of the holding case portion 1b. Thus, the connecting plate 21 is pulled in the direction of the arrow shown in FIG. 2. Further, the base portion of the forked case portion 1c is also brought into contact with the tip of the holding case portion 1b. A stepped wall serving as a stopper is also provided at the fore side of the forked case portion 1c, and a screw ring 28 is engaged with the screw portion of the second cylindrical portion 22b from the fore end. Thus, the forked case portion 1c is pressed against the holding case portion 1b, as shown by the arrow in FIG. 2. Also, the second cylindrical portion 22b protrudes from the forked portion case 1c by a predetermined length, and the base portion of the bending section 2c of the insertion portion 2 is fixedly connected to this protruding portion. The cover member 26, which is fit onto the fore side of the second cylinder portion 22b, protrudes from the fore end of the holder pipe 22 by a predetermined length, and the protruding portions cover the side of the bending section 2c of the insertion portion 2 to the operation unit 1 by a predetermined length. This cover member 26 functions to prevent bucking of the being section 2c.

As can be clearly understood from FIG. 4, the main unit case portion 1a formed of the thick casing is a shell structure configured of a housing 30 having one side portion opened, and a lid 31 connected to this housing 30. By separating the lid 31 from the housing 30, various mechanisms can be mounted to or detached from within the main unit case portion 1a , as well as maintenance such as inspection, repairing or replacing of parts, and so forth. The housing 30 forms the upper plane, lower plane, and one side of the main unit case portion 1a, and operating means each mounted to the main unit case portion 1a are provided to the side of this housing 30. An angle operation device 40 is provided to the housing 30 of the main unit case portion 1a. The angle operation device 40 is for manipulating the angle section 2b of the insertion portion 2.

Figure 7:
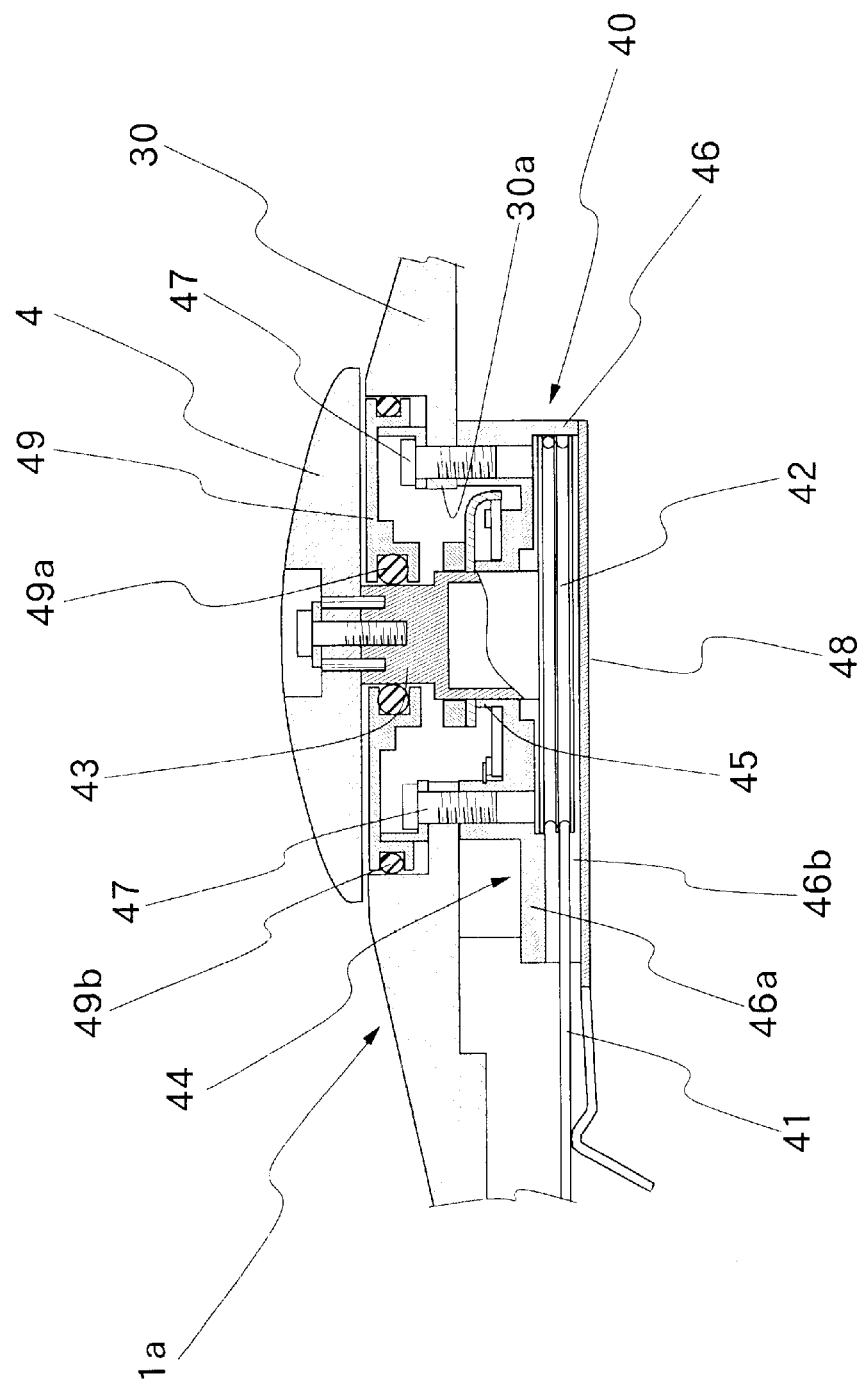
FIG. 7 is a cross-sectional view of the angle operation device.
Figure 8:
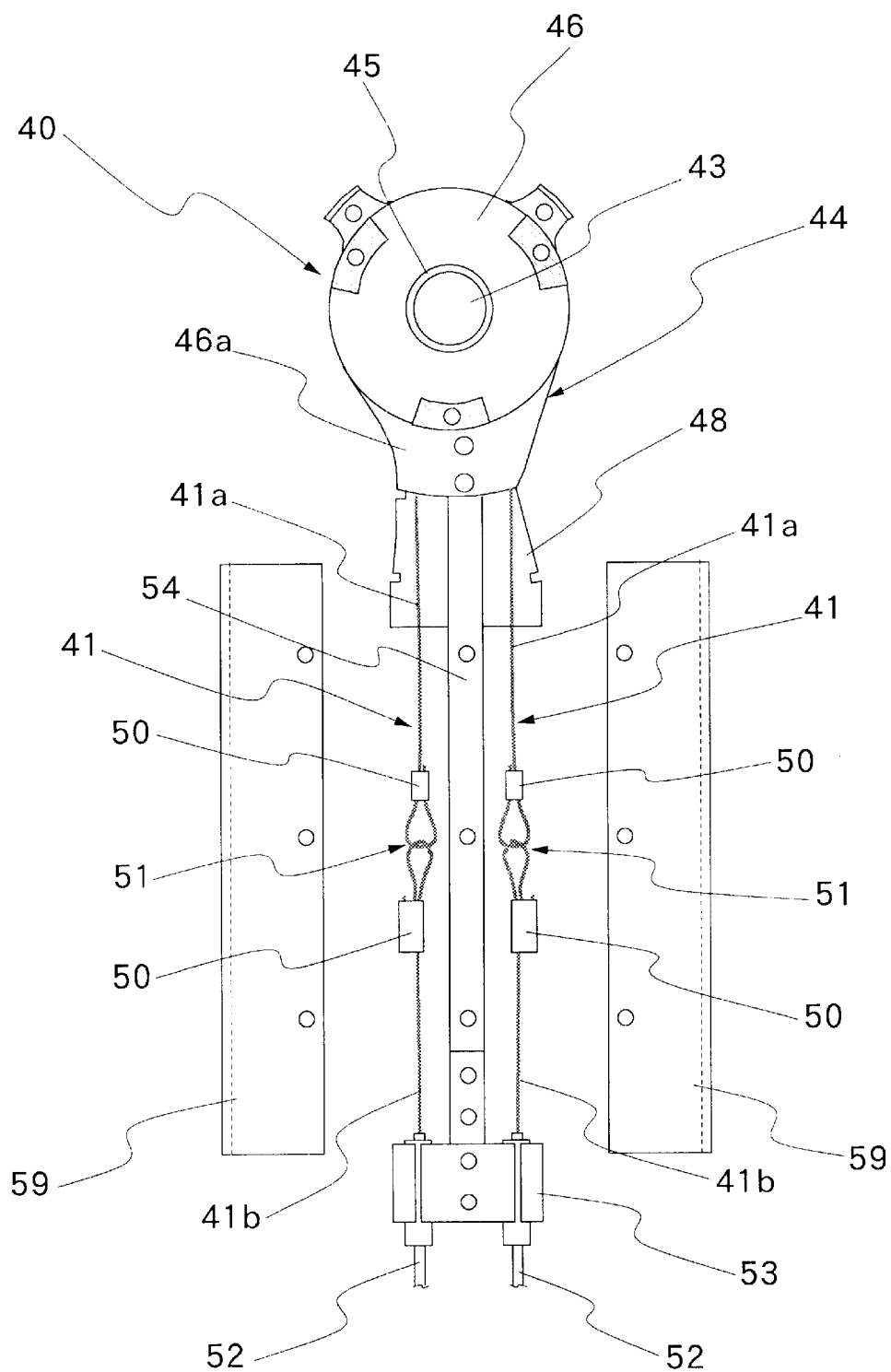
FIG. 8 is a plan view of the angle operation device shown in FIG. 7.

As can be understood from FIG. 7 and FIG. 8, the angle operation device 40 comprises a pulley 42 wound a pair of operating wires 41 and 41 from the angle section 2b or the distal end section 2a, and a rotating shaft 43 coupled to this pulley 42. The rotating shaft 43 is externally extended from a through hole 30a opened in the side of the housing 30, and is linked to the angle operating means 4 such as an operating lever. A recess is formed on the outer periphery of the pulley 42, to allow the operating wire 41 to be taken up by a predetermined length. The angle operating means 4 is formed of a generally L-shaped lever, and the bent portion meandered in the direction of the lower side of the main unit case portion 1a.

The pulley 42 and its rotating shaft 43 are supported by a pulley supporting assembly 44 provided fixedly to the housing 30. The pulley supporting assembly 44 comprises a shaft bearing 45 rotationally supporting the rotating shaft 43, a pulley housing 46 connected to the shaft bearing 45 for covering the greater angle of the pulley 42, and a wire passage 46a as a channel of the operating wires 41 from the pulley 42. The pulley supporting assembly 44 is fixedly held by the housing 30 by bolts 47.

A base plate 48 is then attached to the lower surface of the pulley housing 46. Further provided in the angle operation device 40 is a seal unit 49 to obtain an air tight seal between the inner wall of the through hole 30a of the housing 30 and the outer periphery of the rotating shaft 43. The seal unit 49 has an o-ring 49a for sealing the rotating shaft 43 and an o-ring 49b for sealing the housing 30.

The operating wire 41 is divided into the first wire 41a wound onto the pulley 42, and the second wire 41b running to the angle section 2b. Then, the adjoined ends of the wires 41a and 41b form loops that are fixed by fastening members 50. Operating wire 41 is divided into two and linked to prevent looseness, and the linked loop portion functions serve as the means for preventing looseness. Incidentally, other various configurations may be used for the loose preventing portion.

The greater part of the second wire 41b of the operating wire 41 placed inside the sleeve member forms a control cable. Thus, in the event that the operating wire 41 is pulled, the angle section 2b curves at an angle approximately corresponding to the amount of pulling. The sleeve member has a flexible configuration, such as a tightly coiled wire or a flexible resin sleeve, or the like. However, a hard pipe can be used at a part of the endoscope where there is no bending. Normally, within the bending section 2c, the sleeve member is formed of the tightly coiled wire and the coil is fixedly held at the connecting portion of the bending section 2c to the angle section 2b. Then, only the operating wire 41 is extended through the angle section 2b. The tightly coiled wire is either extended from the bending section 2c to the operation unit 1, or is linked to a sleeve or hard pipe at a position between the bending section 2c and the operation unit 1. In this embodiment, a pipe is connected to the tight coil for the sleeve member.

Now, reference numeral 52 denotes a wire guide pipe as the sleeve member, and the wire guide pipe 52 is fixedly held within the operation unit 1. The operating wire 41 extends from the fixed portion to the angle operation device 40. The length of the operating wire 41 being extended without being covered by the wire guide pipe 52 depends on the length of movement of the means for preventing looseness 51 connecting the first wire 41a and the second wire 41b. In other words, the length must be such that the means for preventing looseness 51 is not caught in the pulley 42 and does not come into contact with the wire guide pipe 52, even in the event that the angle section 2b is curved to the maximum angle.

The end portion of the wire guide pipe 52 is fixed to a pipe holder 53. Therefore, the operating wire 41 is extended so as to pass through this pipe holder 53, and is wound onto the pulley 42. A load based upon the tension of the operating wire 41 is introduced into the pipe holder 53 fixed to the wire guide pipe 52. Therefore, it is necessary that the pipe holder 53 should be stationary and firmly supported in the operation unit 1. The angle operation device 40 and the pipe holder 53 are positioned at distanced locations, specifically, the pipe holder 53 is located in the holding case portion 1b. Now, the pipe holder 53 cannot be mounted directly to the holding case portion 1b which is formed of thin-walled plastic. Since the connecting plate 21 of the connecting member 20 is provided within the holding case portion 1b, the pipe holder 53 might be fixed to this connecting plate 21.

The connecting plate 21 functions to connect the holding case portion 1b and the forked case portion 1a so as to pull in towards the main unit case portion 1a. Therefore, it is necessary to provide strength along the surface of the connecting plate 21. Normally, the thickness of connecting plate 12 is reduced as much as possible to lighten the operation unit 1, so that less force is imposed in the bending direction.

However, there may be great resistance generated when the insertion portion 2 is inserted into the body cavity, thereby applying a bending stress against the operation unit 1. The connecting plate 21 formed of a resilient thin metal plate may be bent or bowed by such the load by virtue of the bending load on the operation unit 1. Of course, once the bending load is relieved, it returns to the original straight state by elastic restoring force. Also, as apparent from FIG. 9, insertion grooves 29 are formed at opposite positions on the inner surface of the holding case portion in order to suppress the deformation of the connecting plate 21 with the load, and extensions 21a are formed on the connecting plate 21 to be inserted into the insertion grooves 29. However, the holding case portion 1b itself is formed of thin plastic material. Therefore, it is not sufficient to hold the connecting plate 21 in stable manner because the holding case portion 1b may bend together with the connecting plate 21 and the like.

When the pipe holder 53 is fixed to the connecting plate 21 which may bend due to the load of the operating wire 41, the position of the pipe holder 53 varies relative to the pulley 42 by the bending load on the main operation unit 1. Consequently, the angle section 2b is unintentionally bent by the extra tension of the operating wire 41 between the introductory portion of the wire guide pipe 52 and the winding portion onto the pulley 42, or otherwise the operating wire 41 is loosened to change the invalid stroke of the angle operating means 4.

To avoid such drawbacks, the pipe holder 53 is attached to the supporting rod 54 at one end, and the other end of the supporting rod 54 is fixed to the pulley supporting assembly 44. Moreover, the supporting rod 54 is extended to the pulley supporting assembly 44 in a state of non-contact with or spaced apart from the connecting plate 21. By this configuration, the angle operation device 40 is supported by the housing 30 together with the pipe holder fixing the end of the wire guide pipe 52 through which the operating wire 41 is passed. Thus, even in the event that the connecting plate 21 deforms, the configuration is not affected in any way.

Figure 9:
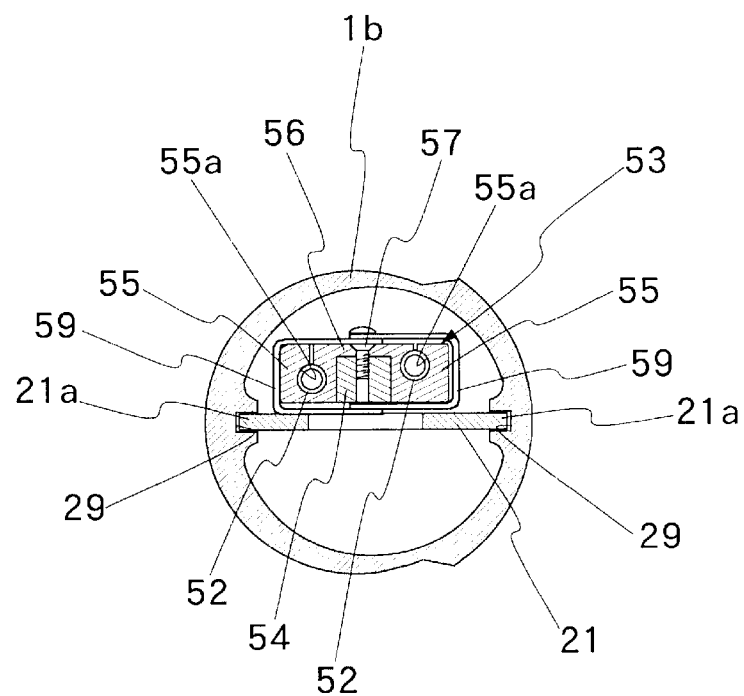
FIG. 9 is a cross-sectional view along line D—D in FIG. 2.
Figure 10:
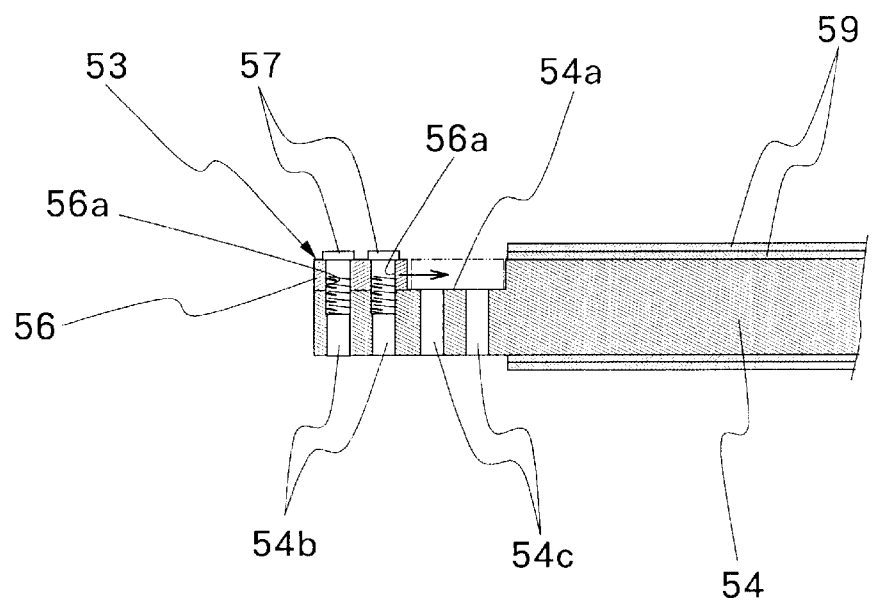
FIG. 10 is a cross-sectional view illustrating the linking portion of the supporting rod and the fastener member.
Figure 11:
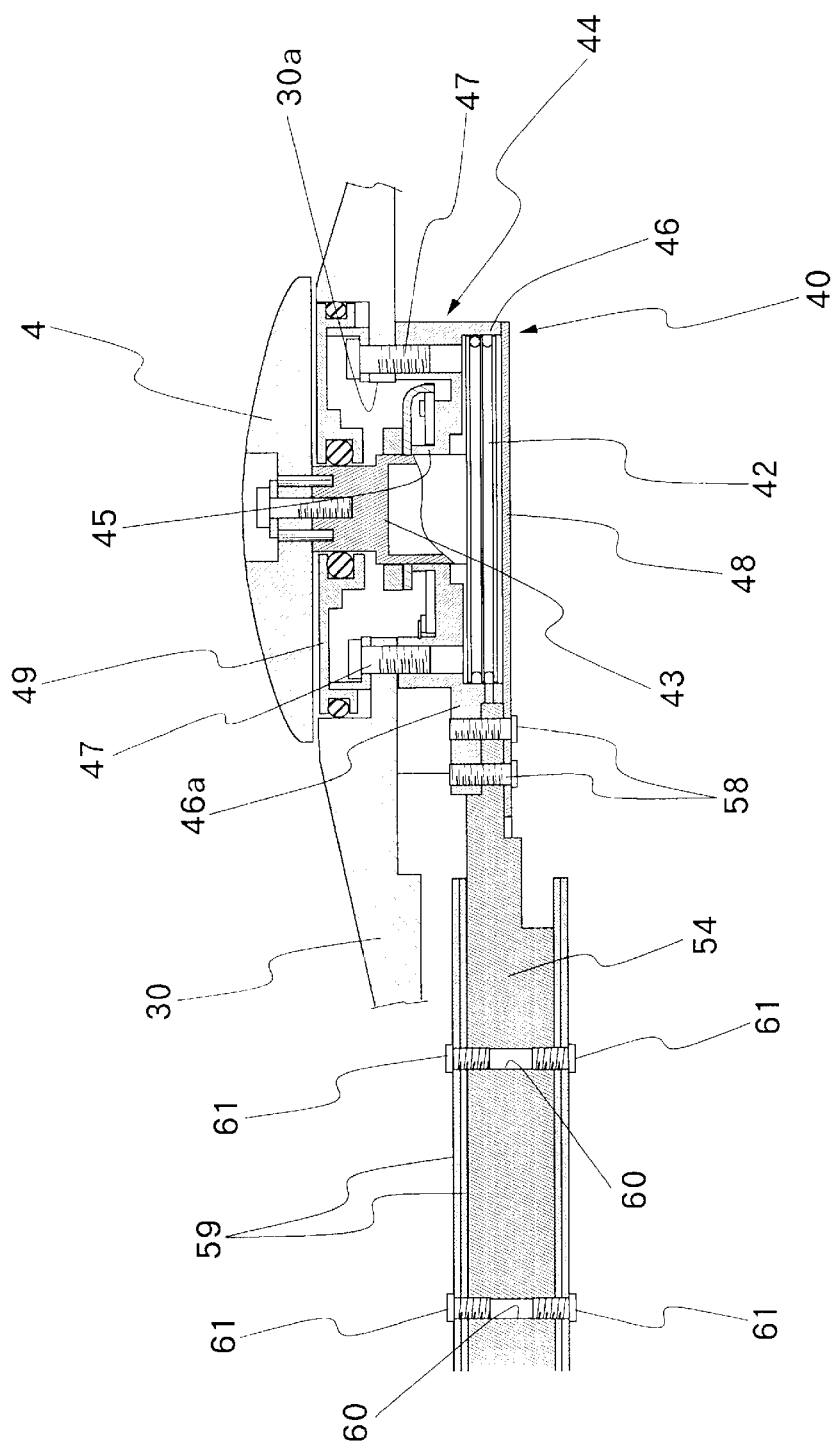
FIG. 11 is a cross-sectional view illustrating the linking portion of the supporting rod and the pulley supporting assembly.

The connected portions between the pipe holder 53 and the supporting rod 54, and between the supporting rod 54 and the pulley supporting assembly 44 are shown in FIG. 10 and FIG. 11. As can be understood from FIG. 9, the pipe holder 53 comprises a pair of wire guide blocks 55 and 55 on the left and right and an interconnecting portion 56 coupled between these wire guide blocks 55 and 55. Through holes 55a are provided to the guide blocks 55, the end of the wire guide pipe 52 is inserted into and secured to the through hole 55a by clamping, soldering, or the like, and then the operating wire 41 is introduced from the wire guide pipe 52. Also, the supporting rod 54 has a shape of a long and narrow rectangular metal bar.

As can be understood from FIG. 10, a recess 54a is formed at the upper plane of the fore side of the supporting rod 54. The pipe holder 53 is straddled on the recess 54a, that is, its interconnecting portion 56 is brought into contact with the upper face of the recess 54a of the supporting rod 54, and the wire guide blocks 55 are placed in contact with both the left and right sides of the supporting rod 54. In order to fix the pipe holder 53, two screw through holes 56a and 56a are bored in the interconnecting portion 56 in the longitudinal direction, and two sets of screw holes, 54b and 54b, and 54c and 54c are also bored in the longitudinal direction on the recess 54a of the supporting rod. The pipe holder 53 is fixed to the supporting rod 54 by two screws, 57 and 57. Of the two sets of screw holes, 54b and 54b, and 54c and 54c, provided separately on the supporting rod 54, the screw holes 54b are the proper mounting position for the pipe holder 53. The other set of screw holes 54c and 54c closer to the base side are provided for extracting the second wire 41b toward the operation unit 1 at the time of linking the loops of the first and second wires 41a and 41b of the operating wire 41. Therefore, the screw holes 54c and 54c do not necessarily have to be provided.

On the other hand, as shown in FIG. 11, the base portion of the supporting rod 54 is fixed to the wire passage 46a on the pulley supporting assembly 44. Now, both side portions of the wire passage 46a have partitions 46b for sectioning off paths for the operating wires 41 and 41 (see FIG. 7), and the supporting rod 54 is fixed to the partition 46a by two screws 58. Therefore, the operating wire 41 is guided following the side surface of the supporting rod 54 through the paths on either side of the wire passage 46a, and is led into the through holes 55a of the wire guide blocks 55 on the pipe holder 53.

The operating wire 41 is extended along the side face of the supporting rod 54, and the means for preventing looseness 51 is provided at this position. Also, in the operation unit 1, other guide members are provided, such as fragile members like the light guide to a near position of the operating wire 41. When the operating wire 41 is subject to pushing and pulling, the wire loop portion as the means for preventing looseness 51 and their fastening member 50 are brought in contact with other members and are brought to sliding engagement with these members, resulting in damage to the other members. In order to prevent such damage, a wire cover 59 is mounted to both left and right sides of the supporting rod 54 in the moving range of the means for preventing looseness 51 of the operating wire 41.

As can be understood from FIG. 8 and FIG. 9, the wire covers 59 are formed by bending a thin metal plate into a generally box-shaped form with one side opened, and these wire covers 59 are configured such that their opened upper and lower surfaces face the left and right side lateral faces of the supporting rod 54. Also, one of the wire covers 59, either the left or right, is fit with the upper and lower faces of the supporting rod 54 to overlap on the opposite side wire cover 59. Thus, a tunnel-shaped path over the entire length of this supporting rod 54 is formed between the left and right side lateral walls of the supporting rod 54 and the wire covers 59. This path is formed so as to have a cross-sectional area large enough to allow easy movement of the means for preventing looseness 51 and fastening members 50 of the operating wire 41.

Both wire covers 59 and 59 are detachably fixed to the supporting rod 54. To this end, multiple bolt through holes 60 are bored along the overlapping portions of both wire covers 59, 59 and the supporting rod 54 in the axial direction at a predetermined pitch, and screwing bolts 61 and 61 are fixed from above and below of these bolt through holes 60. The wire covers 59 are not in contact with the connecting plate 21 of the connecting member 20. On the connecting plate 21, punch-out portions are formed to reduce the weight, and the above bolts 61 are fitted in these punch-out portions. Therefore, the screwing and unscrewing of these bolts 61 can be performed via the punchout portions.

With the foregoing configurations, all mechanisms related to the angle operation are ultimately supported by the main unit case portion 1c, and are held not in contact with the connecting plate 21 making up the connecting member 20, which may bend under load. Thus, in the event that a bending load or the like acts upon the operation unit 1, there is no change in the tension of the operating wire 41. Consequently, there is no change of the angle section 2*b* in the direction bending unless the angle operation is carried out unintentionally, and also in arrangements wherein the angle operating means 4 maintains constantly a predetermined amount of invalid stroke, where given it.

Now, the long supporting rod 54 should be reduced in its size in order to enlarge the space within the operation unit 1. However, the force acting on the supporting rod 54 is only the operating reaction force at the time of pushing and pulling the operating wire 41. At that time, the load is subjected to the supporting rod 54 in the axial direction, and there is no bending load or the like. The supporting rod 54 has extremely great strength in the axial direction, and will not be deformed, provided that the stress is exerted in the bending direction. Therefore, the supporting rod 54 can maintain an extremely stable form. From this point as well, there is no possibility to change its tension for the operating wire 41, and the angle operation can be conducted in an excellent manner.

Although the portion of the operating wire 41, specifically where the means for preventing looseness 51 is provided, runs within the tunnel-shaped path defined by the wire cover 59, the wire covers 59 which are fixed to the supporting rod 54 with the bolts 61 can be easily separated from the supporting rod 54 by removing the bolts 61. Over a long period of time, the operating wire 41 is elongated or broken as a result of the great tension it undergoes. Therefore, it is necessary to perform maintenance such as repairing or replacing the operating wire 41. The wires 41*a* and 41*b* can be separated for the maintenance purposes by releasing one of the loops at the linked portion with the loops for forming the loose preventing portion 51. Thus, the removability of wire covers 59 from the supporting rod 54 facilitates ease of the maintenance work.

For example, in a case of replacement of the second wire 41*b* to the angle section 2*b*, the fastening member 50 forming the loop is separated from the second wire 41*b*. When reassembling the operating wire 41, the tip end of the second wire 41*b* is passed through the loop formed of the first wire 41*a*. Then, a loop is formed at an appropriate position on the side of the second wire 41*b*, and finally the edge of the loop is fixed by means of the fastening member 50 again. For the sake of this work in a facilitated manner, the new second wire 41*b* should be approached as close as possible to the loop of the first wire 41*a*. The surplus length is given for the second wire 41*b* within the insertion portion 2 in order to suppress resistance upon bending of the insertion portion 2, particularly to minimize the resistance of the bending section 2*a*. Therefore, at the time of maintenance, the pipe holder 53 can be pulled into the operation unit 1 together with the second wire 41*b* in the tightly coiled wire.

The two fixing positions for the pipe holder 53 are given in the axial direction of the supporting rod 54 and the interconnecting portion 56 of the pipe holder 53 can be slid in the direction of the arrow of the FIG. 10 for this purpose. Also, the screw through holes 56*a* are positioned so as to match the screw holes 54*c* at the base side of the supporting rod 54, allowing screws 57 to be screwed in. Consequently, as shown by phantom lines in the same figure, the pipe holder 53 can be brought close to the first wire 41*a*. That is to say, the tip of the second wire 41*b* can be brought near the loop of the first wire 4l*a*, along with the wire guide pipe 52. Therefore, the task of passing the end thereof through the loop of the first wire 41*a* and the task of fixing to the fastening member 50 which fixes the end thereof with soldering and the like can be easily performed. After the completion of this work, the screws 57 are removed and then the pipe holder 53 is shifted to the solid line position shown in FIG. 10, thus allowing it to be fixed again by means of the screws 57. Thereby, the pipe holder 53 is fixed in the proper position, and the extra length is returned into the insertion portion 2.

Meanwhile, the operating wire 41 is divided into the first wire 41*a* and the second wire 41*b* bridged by the means for preventing looseness 51 for achieving the smooth movement of the operating wire 41 at the time of angle operation. That is to say, at the time of angle operation, one of the pair of operating wires 41 and 41 is wound onto the pulley 42, and the other is fed out from the pulley 42. The tension acts on the operating wire 41 at the winding part, while the feeding part of the operating wire 41 may not be pushed out to the tip end due to sliding resistance and the like within the sleeve members. In such an event, excess length of the operating wire 41 is left between the winding portion to the pulley 42 and the wire guide pipe 52. The means for preventing looseness 51 can absorb the excess length, thereby allowing the operating wire 41 to move smoothly.

Figure 12:
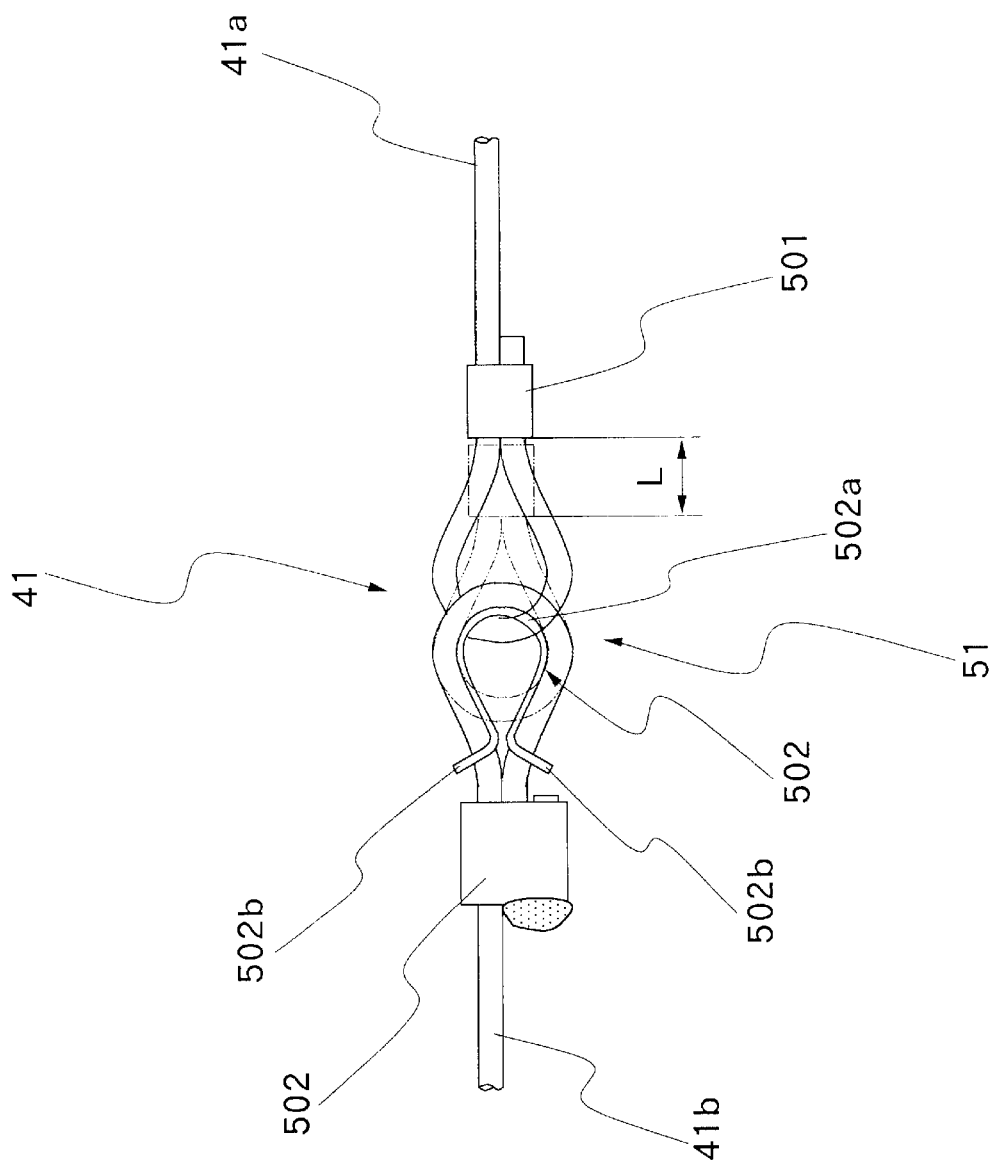
FIG. 12 is an enlarged view illustrating the linking portion of the first wire and second wire of the operating wires.
Figure 13:
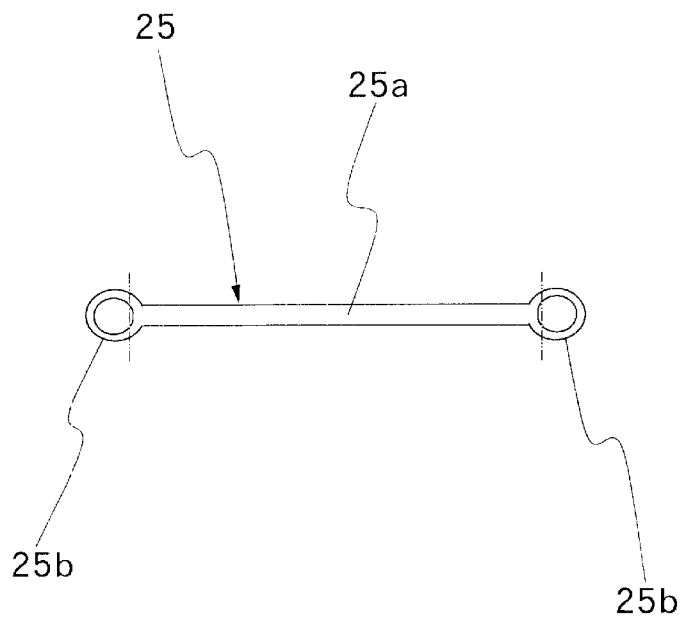
FIG. 13 is a plan view of the elastic plate piece.
Figure 14:
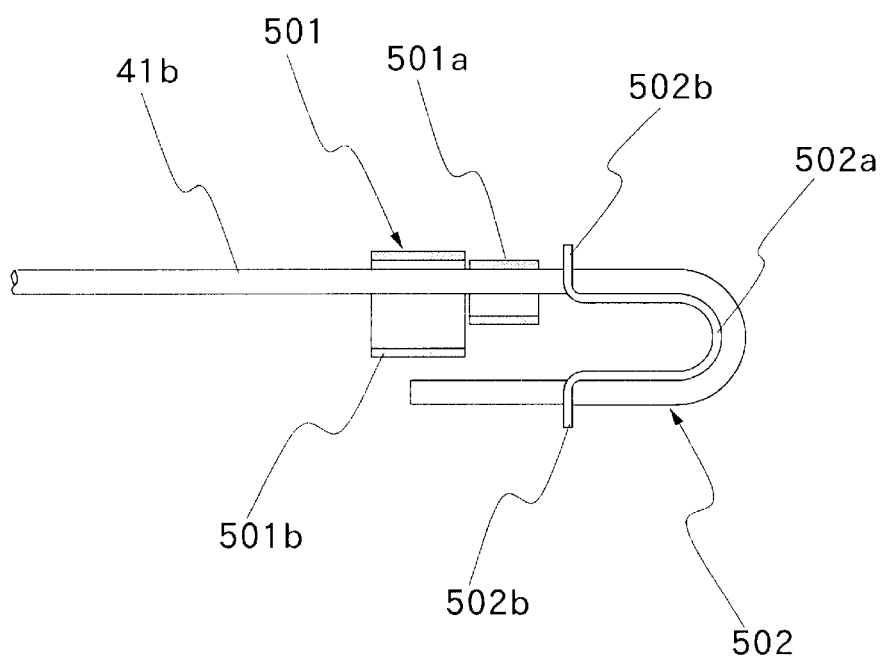
FIG. 14 is an explanatory diagram illustrating the end fixing state of the operating wires in the state of the elastic plate piece being mounted.

Now, a specific structure of the loose preventing portion 51 is shown in FIG. 12 through FIG. 14. As can be clearly understood from these diagrams, the linking portion of the first wire 41*a* and the second wire 41*b* of the operating wire 41 are linked in chain fashion by forming loops at each end portion. Then, the ends of the loops are fixed by clamping with fasteners 501 and 502 constituting the fastening members 50. As can be understood from FIG. 12, the first wire 41*a* has been looped, and then the end is fixed with the fastener 501. On the other hand, the second wire 41*b* has at its inner side an elastic plate piece 502 serving as a loop maintainer piece, and the edge is fixed folding the end back twice. Therefore, as shown in FIG. 14, the fastener 501 is configured of a first fastening portion 501*a* where two wires are passed through, and a second fastening portion 501*b* where the wire in the state of being folded back again is inserted along with the first fastening portion 501*a*. Note that the elastic plate piece may be provided to the side of the first wire 41*a*, or to both.

The elastic plate piece 502 is composed of a main spring piece 502*a* having a long, slender and resilient thin metal piece, and mounting sections 502*b* and 502*b* formed on both ends of this main spring piece 502*a*. Each of the mounting sections 502*b* is broadened from the main pieces 502*a* and forms a through hole having great diameter portions so that the second wire 41*b* may be loosely inserted. Assembling the elastic plate piece 502 to the second wire 41*b* allows the loop of the second wire 41*b* to be maintained at a constant form, i.e., a form essentially close to a true circle.

Consequently, the looped portions of the first and second wires 41*a* and 41*b* are maintained in an extremely stable state. Changing the degree of overlapped length of the loops absorbs the slack in the operating wire 41. That is, as shown in FIG. 12, the length of the linked portion of the wire can be changed by an amount L, between the minimum overlapped state of the two loops (state shown by solid lines) and the maximum overlapped state (state shown by phantom lines). This amount of change in length is the slack absorbing length for the operating wire 41.

Also, the area between the winding portion to the pulley 42 to the wire guide pipe 52 must be extended as straight as possible to assure smooth movement of the operating wire 41. The wire guide pipe 52, which guides the operating wire 41 to the insertion portion 2, is preferably placed as close as possible to the placement position of the operating wire 41 within the insertion portion 2. By contrast, the angle operation device 40 to which the pulley 42 is mounted is preferably placed at a position near the inner surface of the housing 30 of the main unit case 1a, taking into consideration the insertion members such as the light guide and fluid channel. The positions of the pulley 42 become offset from wire guide pipe 52.

Figure 15:
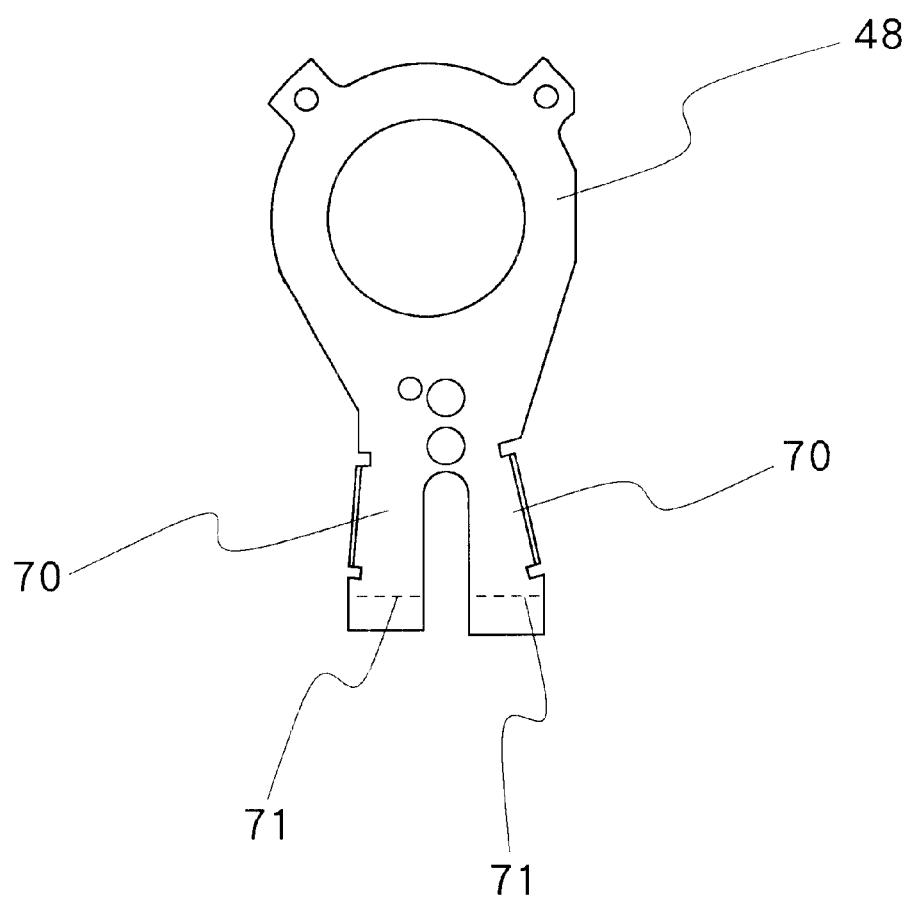
FIG. 15 is a plan view of the base plate provided integrally with a spring-shaped plate piece.
Figure 16:
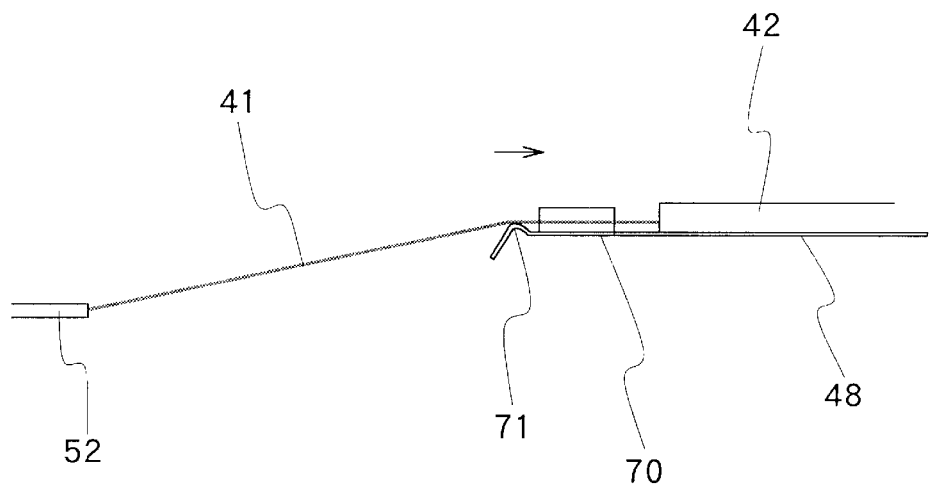
FIG. 16 is an explanatory diagram illustrating the operating wire path from the angle operation device to the wire guide pipe.
Figure 17:
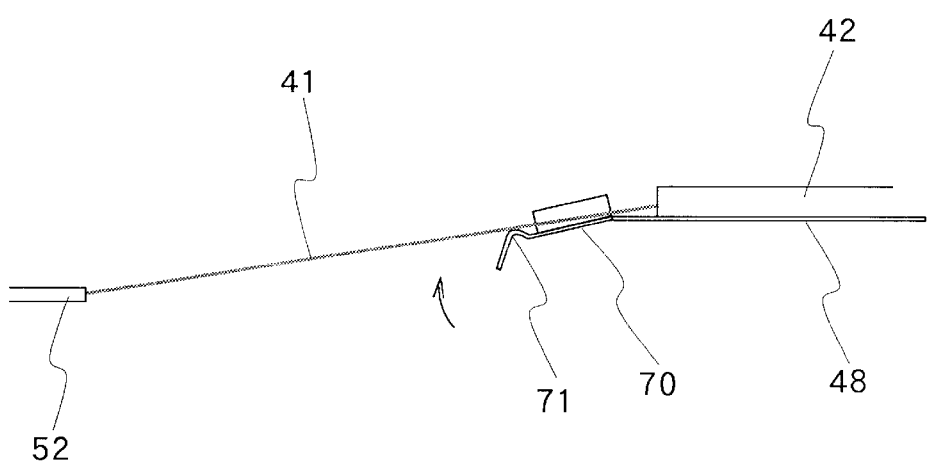
FIG. 17 is an operation explanatory diagram illustrating a state wherein resistance is incurred in the operating wire path shown in FIG. 16, due to manipulation of the operating wires.

The operating wire 41 is laid in a non-restricted state between the pulley 42 and the wire guide pipe 52. Therefore, in the event that the pulley 42 is positioned far from the wire guide pipe 52, the operating wire 41 is inclined at an angle according to the magnitude of the offset. Therefore, force other than in the winding direction acts at the time of taking up the operating wire 41, increasing the load from operation on the angle operating means 4, thereby loosening the stability of the winding portion of the operating wire 41 to the pulley 42. In order to suppress the inclination angle of the operating wire 41 based on the offset between the pulley 42 and the wire guide pipe 52, a configuration such as shown in FIG. 15 through FIG. 17 is used.

That is, the base plate 48 covering the bottom of the pulley 42 has resilient plate pieces 70 which are placed along with the left and right sides of the supporting rod 54, and protrusions 71 are provided to these resilient plate pieces 70. The protrusions 71 can be formed by a pressing means or the like to form a convex shape upwardly toward the extending direction of the operating wire 41. In a case where there is no particularly great force acting on the operating wire 41, as shown in FIG. 16, the upper plane of the protrusions 71 are brought in contact with the operating wire 41 from the recessed groove of the pulley 42. Thereby, the operating wire 41 is extended at a position extended almost completely straight from the pulley 42. By adopting the foregoing construction, although there is difference in height between the wire guide pipe 52 connected to the pipe holder 53 and the pulley 42, the operating wire 41 can be supported by the protrusion 71 on the resilient plate piece 70, and can be pushed upwards so as to be held in an approximately straight way in a predetermined length running from the wire passage 46a. Consequently, as shown in the figure by the arrow, the operating wire 41 is dragged into the pulley 42 in a straight manner at the time for pulling operation of the operating wire 41 toward the pulley 42 with little load without forcing the operating wire 41 away from the pulley 42.

Such construction increases sliding resistance at the entrance of the guide pipe 52 by the winded angle of the operating wire. However, the protrusion 71 which supports the operating wire 41 at a straight state near the pulley 42 is held in a substantially floating state by the resilient plate piece 70. Therefore, because a great load acts on this protrusion 71, the entire resilient plate piece 70 cannot be deformed in the direction of sinking. As a result, as shown in FIG. 17, the angle of the operating wire 41 at the entrance of the wire guide pipe 52 is relieved so as to reduce the sliding resistance at its portion and to make the operating wire 41 move easily. Moreover, by the resilient plate piece 70 exhibiting elastic deformation, the side where the pulley 42 is mounted becomes the fulcrum and curves downwards. Consequently, as shown by the arrow in FIG. 17, pressing force acts on the resilient plate piece 70, in the direction of being flapped. Because the force for flapping the resilient plate piece 70 is exerted to the operating wire 41 to the direction of the pulley 42 side, it the winding of the operating wire 41 wound onto the pulley 42 proceeds smoothly. operating wire 41 easy movement. Moreover, by the resilient plate piece 70 exhibiting elastic deformation, the side where the pulley 42 is mounted becomes the fulcrum and curves downwards consequently, as shown by the arrow in FIG. 17 pressing force acts on the resilient plate piece 70, in the direction of being flapped. Because the urging force for flapping the resilient plate piece 70 is exerted to the operating wire 41 to the direction of the pulley 42 side, it assures to proceed smoothly the winding of the operating wire 41 wound onto the pulley 42.

What is claimed is:

1. A manipulation mechanism for an angle section of an endoscope, comprising a main operation unit and an insert portion connected to said main operation unit, said insert portion having a distal end section connected with said angle section, adapted for manipulating to curve said angle section by pulling and pushing at least a pair of operating wires running throughout said insert portion and introduced into said main operation unit, wherein said manipulation mechanism comprises:

at least one pulley provided within said main operation unit, with the base of said operating wires wound thereupon;

a pulley rotating shaft extended externally from a casing of said main operation unit to rotate said pulley;

an angle operating means provided outside of said main operation unit and coupled to said pulley rotating shaft;

a pulley supporting assembly fixedly held by said casing of said main operation unit, for supporting said pulley to be reciprocally rotated over a predetermined angle;

a sleeve member provided within said main operation unit for passing through said operating wires from said pulley;

a pipe holder fixedly mounted to said sleeve member;

a supporting rod connected at one end to said pulley supporting assembly and fixed to said pipe holder at the other end, wherein said casing of said main operation unit comprises a main unit and a holding case portion assembled by a connecting member, and at least said angle operation means is supported by said main unit case, and said pipe holder and said supporting rod are placed without contacting said connecting member.

2. A manipulation mechanism for an angle section of an endoscope according to claim 1, wherein a wire cover is detachably mounted to said supporting rod to form a passage in the form of a tunnel for running said operating wire along a side lateral face of said supporting rod.

3. A manipulation mechanism for an angle section of an endoscope according to claim 1, wherein said pulley supporting assembly comprises a bearing for rotatably supporting said pulley rotating shaft;

a pulley housing for covering said pulley; and a wire passage for orienting said operating wires from said supporting rod pulley, wherein said is connected to said wire passage.

4. A manipulation mechanism for an angle section of an endoscope according to claim 3, wherein said pipe holder is detachably fixed to said supporting rod by a screw.

5. A manipulation mechanism for an angle section of an endoscope according to claim 4, wherein said supporting rod has at least two fixing portions to which said pipe holder is screwed at different positions in the axial direction thereof.

6. A manipulation mechanism for an angle section of an endoscope according to claim 3, wherein said wire passage of said pulley supporting assembly has a wire carrier for elastically supporting said operating wire in an approximately straight manner at a predetermined length from said pulley.

7. A manipulation mechanism for an angle section of an endoscope according to claim 6, wherein said wire carrier is integrally form with a base cover of said pulley cover.

8. A manipulation mechanism for an angle section of an endoscope, comprising a main operation unit and an insert portion connected to said main operation unit, said insert portion having a distal end section connected with said angle section, adapted for manipulating to curve said angle section by pulling and pushing at least a pair of operating wires running throughout said insert portion and introduced into said main operation unit, wherein said manipulation mechanism comprises:

- at least one pulley provided within said main operation unit, with the base of said operating wires wound thereupon;
- a pulley rotating shaft extended externally from a casing of said main operation unit to rotate said pulley;
- an angle operating means provided outside of said main operation unit and coupled to said pulley rotating shaft;
- a pulley supporting assembly fixedly held by said casing of said main operation unit, for supporting said pulley to be reciprocally rotated over a predetermined angle;
- a sleeve member provided within said main operation unit for passing through said operating wires from said pulley;
- a pipe holder fixedly mounted to said sleeve member;
- a supporting rod connected at one end to said pulley supporting assembly and fixed to said pipe holder at the other end, and
- wherein a wire cover is detachably mounted to said supporting rod to form a passage in the form of a tunnel for running said operating wire along a side lateral face of said supporting rod, and
- wherein said wire cover comprises a generally box-shaped plate that is open at one end, a pair of plates being fit together from either side lateral wall of said supporting rod to form said passage between said wire covers and said side lateral face of said supporting rod, with which both wire covers are overlapped for securing to said supporting rod simultaneously by screws.

9. A manipulation mechanism for an angle section of an endoscope, comprising a main operation unit and an insert portion connected to said main operation unit, said insert portion having a distal end section connected with said angle section, adapted for manipulating to curve said angle section by pulling and pushing at least a pair of operating wires running throughout said insert portion and introduced into said main operation unit, wherein said manipulation mechanism comprises:

- at least one pulley provided within said main operation unit, with the base of said operating wires wound thereupon;
- a pulley rotating shaft extended externally from a casing of said main operation unit to rotate said pulley;
- an angle operating means provided outside of said main operation unit and coupled to said pulley rotating shaft;
- a pulley supporting assembly fixedly held by said casing of said main operation unit, for supporting said pulley to be reciprocally rotated over a predetermined angle;
- a sleeve member provided within said main operation unit for passing through said operating wires from said pulley;
- a pipe holder fixedly mounted to said sleeve member;
- a supporting rod connected at one end to said pulley supporting assembly and fixed to said pipe holder at the other end,
- wherein said operating wire comprises a first wire wound onto said pulley, and a second wire running from said insertion portion, and
- wherein said first and second wires are looped at one end to link each other by means of fastener members within said wire covers.

10. A manipulation mechanism for an angle section of an endoscope according to claim 9, wherein one of said loops has a retaining plate along the inner periphery thereof to keep a constant shape of said loop, and the other loop is brought into contact with said retaining plate.

11. A manipulation mechanism for an angle section of an endoscope according to claim 10, wherein said retaining plate is formed by a resilient metal plate to keep said loop in said shape, said retaining plate has provided at both ends through holes for receiving said wire, and said fastener member is fixed near said retaining plate.

12. A manipulation mechanism for an angle section of an endoscope according to claim 11, wherein said resilient metal plate has, along its width direction, a concave curve on the surface opposite to said operating wire.

13. A manipulation mechanism for an angle section of an endoscope, comprising a main operation unit and an insert portion connected to said main operation unit, said insert portion having a distal end section connected with said angle section, adapted for manipulating to curve said angle section by pulling and pushing at least a pair of operating wires running throughout said insert portion and introduced into said main operation unit, wherein said manipulation mechanism comprises:

- at least one pulley provided within said main operation unit, with the base of said operating wires wound thereupon;
- a pulley rotating shaft extended externally from a casing of said main operation unit to rotate said pulley;
- an angle operating means provided outside of said main operation unit and coupled to said pulley rotating shaft;
- a pulley supporting assembly fixedly held by said casing of said main operation unit, for supporting said pulley to be reciprocally rotated over a predetermined angle;
- a sleeve member provided within said main operation unit for passing through said operating wires from said pulley;
- a pipe holder fixedly mounted to said sleeve member;
- a supporting rod connected at one end to said pulley supporting assembly and fixed to said pipe holder at the other end,
- wherein said pulley supporting assembly comprises a bearing for rotatably supporting said pulley rotating shaft;
- a pulley housing for covering said pulley; and
- a wire passage for orienting said operating wires from said pulley,
- wherein said supporting rod is connected to said wire passage,
- wherein said wire passage of said pulley supporting assembly has a wire carrier for elastically supporting said operating wire in an approximately straight manner at a predetermined length from said pulley, and
- wherein said wire carrier is formed of a convex protrusion on a resilient plate.

* * * * *

UNITED STATES PATENT AND TRADEMARK OFFICE
CERTIFICATE OF CORRECTION

PATENT NO. : 6,491,627 B1
DATED : December 10, 2002
INVENTOR(S) : Komi

It is certified that error appears in the above-identified patent and that said Letters Patent is hereby corrected as shown below:

<u>Title page,</u>
Item [30], Foreign Application Priority Data, should read:

-- (30)  Foreign Application Priority Data

Aug. 18, 1999 (JP)………..………...11-231237
    Aug. 18, 1999 (JP)………..………...11-231238
    Aug. 18, 1999 (JP)………..………...11-231239 --

Signed and Sealed this

Twenty-ninth Day of April, 2003

JAMES E. ROGAN
*Director of the United States Patent and Trademark Office*